United States Patent
Bisrat et al.

(10) Patent No.: US 6,461,642 B1
(45) Date of Patent: Oct. 8, 2002

(54) CRYSTALLIZATION USING SUPERCRITICAL OR SUBCRITICAL FLUIDS

(75) Inventors: Mikael Bisrat, Strängnäs (SE); Saeed Moshashaee, Stockholm (SE); Håkan Nyqvist, Tullinge (SE); Mustafa Demirbüker, Järfälla (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/486,689

(22) PCT Filed: Nov. 22, 1999

(86) PCT No.: PCT/SE99/02153

§ 371 (c)(1),
(2), (4) Date: Mar. 1, 2000

(87) PCT Pub. No.: WO00/30613

PCT Pub. Date: Jun. 2, 2000

(30) Foreign Application Priority Data

Nov. 23, 1998 (SE) ................................................ 9804001

(51) Int. Cl.⁷ .............................. A61K 9/14; B29B 9/00
(52) U.S. Cl. ........................ 424/489; 424/400; 424/484; 514/951; 264/5; 264/6; 264/11
(58) Field of Search ................................. 424/400, 439, 424/484, 488, 489, 499; 514/826, 926, 951, 964; 128/200.14; 264/5, 6, 11

(56) References Cited

U.S. PATENT DOCUMENTS

| 5,043,280 A | * | 8/1991 | Fischer et al. ........... 435/235.1 |
| 5,301,664 A | * | 4/1994 | Sievers et al. ......... 128/200.23 |
| 5,770,559 A | * | 6/1998 | Manning et al. ................ 514/2 |
| 5,851,453 A | * | 12/1998 | Hanna et al. ................... 264/5 |
| 6,095,134 A | * | 8/2000 | Sievers et al. ......... 128/200.14 |
| 6,126,919 A | * | 10/2000 | Stefely et al. ................ 424/45 |

* cited by examiner

Primary Examiner—Thurman K. Page
Assistant Examiner—Charesse Evans
(74) Attorney, Agent, or Firm—White & Case LLP

(57) ABSTRACT

The invention provides a process for preparing essentially crystalline particles containing a substance in solvated form, by dissolving the substance in a first solvent, introducing the solution and a supercritical or subcritical fluid into an apparatus, wherein the fluid contains an anti-solvent and a second solvent, which is water. Preferably, the anti-solvent is carbon dioxide which is totally saturated with the second solvent, which is water. The invention further provides formulations comprising particles produced according to the present process containing one or more pharmacologically active substances and one or more pharmaceu-tically acceptable excipients, use of said formulations in the treatment of an allergic and/or inflammatory condition of the nose or lungs and methods for treatment of such conditions.

42 Claims, No Drawings

CRYSTALLIZATION USING SUPERCRITICAL OR SUBCRITICAL FLUIDS

FIELD OF THE INVENTION

The present invention is directed to a process for preparing essentially crystalline particles containing a substance in a solvated form, the resulting particles being useful e.g. for oral or nasal inhalation.

BACKGROUND OF THE INVENTION

The increasing production and use of fine powders in the pharmaceutical industry has high-lighted the need for reliable methods for assessing their physicochemical and technical handling. Particles obtained by spray drying, freeze drying, rapid solvent quenching or from controlled precipitation will often be in an amorphous state or in a meta-stable crystalline form. For crystalline substances, a diminution operation, e.g. micronization, will give particles with amorphous regions.

The usefulness of amorphous and/or meta-stable crystalline particles is limited due to their thermodynamic instability. For example, such particles tend to fuse in the presence of moisture, thereby forming hard agglomerates which are difficult to break up. Furthermore, amorphous and/or meta-stable crystalline particles exhibit larger batch-to-batch variations as regards bulk density than do well-defined crystalline particles. This may cause problems e.g. in inhalers for treating respiratory disorders, due to lower dosing accuracy.

It is therefore desirable to produce crystalline or at least essentially crystalline particles, which exhibit a good dosing accuracy and storage stability.

Methods to convert the amorphous or meta-stable crystalline particles into crystalline particles are known. Examples are disclosed in U.S. Pat. Nos. 5,709,884 and 5,562,923 both to Astra AB of Sweden.

The known methods to produce crystalline particles are, however, often time consuming requiring substantial space. Therefore, there is a need for a more efficient technique for producing crystalline particles with a high shelf life.

SUMMARY OF THE INVENTION

The object of the present invention is to provide a process for preparing essentially crystalline particles containing a substance in a solvated form, comprising dissolving the substance in a first solvent, introducing into an apparatus under supercritical or subcritical conditions the solution containing the substance with an anti-solvent and a second solvent, which is water and recovering the essentially crystalline particles formed containing the substance in a solvated form.

According to a preferred embodiment of the invention, the anti-solvent is carbon dioxide.

According to another preferred embodiment, the relative solvent saturation of the anti-solvent lies in the range of from 15% up to 50% of total solvent saturation at the prevailing pressure and temperature.

DETAILED DESCRIPTION OF THE INVENTION

The present invention relates to a process for preparing essentially crystalline particles containing a substance in a solvated form, comprising (a) dissolving the substance in a first solvent;

(b) introducing into an apparatus the solution containing the substance together with a supercritical or subcritical fluid comprising an anti-solvent and a second solvent which is water, and (c) recovering the essentially crystalline particles formed.

The inventors of the present process, have surprisingly found that by applying a supercritical or subcritical fluid comprising an anti-solvent and a second solvent, which is water to a solution containing the substance at issue, essentially crystalline particles can be obtained. This is especially true if the particles are post-conditioned with the supercritical or subcritical fluid.

The process of the present invention can be performed in accordance with fluid gas anti-solvent techniques, wherein fluid gas includes material in its supercritical, near critical and subcritical states as well as compressed gases. Suitable fluid gas anti-solvent techniques, include but are not limited to, GAS (gas anti-solvent precipitation), a modified version of the GAS technique known as SEDS (solution enhanced dispersion by supercritical fluid), ASES (aerosol solvent extraction system), SAS (supercritical anti-solvent) and PCA (precipitation with compressed fluid anti-solvent). Preferably use is made of the SEDS technique.

The traditional SEDS technique employs an apparatus comprising a particle-forming vessel with means for controlling the temperature and pressure of said vessel, together with a means for co-introduction into said vessel of a supercritical or subcritical fluid and a vehicle containing at least one substance in solution or suspension, such that dispersion and extraction of the vehicle occur simultaneously by the action of the fluid.

To make the present invention work, especially if it is performed in accordance with the SEDS technique, the following criteria apply to the combination of first solvent, second solvent, anti-solvent, and the substance at issue:

i) the substance at issue must be essentially soluble in the first solvent, ii) the first solvent must be miscible with the anti-solvent, e.g. carbon dioxide, iii) the second solvent must be miscible with the anti-solvent, iv) the substance at issue should be insoluble in the anti-solvent, v) the amount of second solvent in the anti-solvent must not exceed that needed for saturating the supercritical or subcritical anti-solvent.

The latter criterion is essential for avoiding formation of a two-phase system containing supercritical solvent-saturated anti-solvent, e.g. water-saturated carbon dioxide, and a liquid phase containing e.g. water, solvent and dissolved active substance.

In the SEDS technique, the substance at issue is dissolved in the solvent and co-introduced into an apparatus via a nozzle having at least two channels, one channel for a solvent and one channel for an anti-solvent i.e. the supercritical or subcritical fluid. Mixing and dispersion occur at the spot where the fluids meet. The supercritical fluid dissolves the solvent but not the substance since the substance must be insoluble in the anti-solvent. Therefore, the substance will precipitate as particles with a suitable size.

A suitable apparatus for the SEDS process is described in WO 95/01221. The SEDS technique is further described in WO 96/00610. WO 95/01221 and WO 96/00610 (both to the University of Bradford, GB), are hereby incorporated by reference.

A "supercritical fluid" is a fluid at or above its critical pressure ($P_c$) and critical temperature $T_c$) simultaneously. Supercritical fluids also encompass "near supercritical fluids", which are above but close to its critical pressure ($P_c$) and critical temperature $T_c$) simultaneously. A "subcritical fluid"0 is above its critical pressure ($P_c$) and close to its critical temperature ($T_c$).

The anti-solvent is suitably one or more of carbon dioxide, nitrous oxide, sulfur hexafluoride, ethane, ethylene, propane, n-pentane, xenon, trifluoromethane, chlorotrifluoromethane, a fluorocarbon compound, a chlorofluorocarbon compound, nitrogen, or water. The anti-solvent is preferably carbon dioxide.

In the present invention, the supercritical or subcritical fluid contains an anti-solvent and a second solvent, which is water, is miscible with said anti-solvent.

Immediately before the supercritical or subcritical fluid is introduced in the particle-forming vessel, the relative solvent saturation of the anti-solvent may be in the range of from about 50% up to 100%, i.e. total, solvent saturation at the prevailing pressure and temperature. Immediately before treating the particles in the conditioning vessel, the relative solvent saturation of the anti-solvent is suitably in the range of from 70% up to 100%, preferably from 90% up to 100%, and more preferably from 95% up to 100% of total solvent saturation at the prevailing pressure and temperature.

A particularly preferred combination of anti-solvent and solvent is carbon dioxide and water, advantageously when the relative water-saturated supercritical carbon dioxide (RWSSC) lies in the range of from about 50% up to 100%, i.e. total saturation, especially when the RWSSC lies in the range of from 90% up to 100%, and more especially when the RWSSC lies in the range of from 95% up to 100% of total solvent saturation at the prevailing pressure and temperature.

The flow rate ratio between dry and totally solvent saturated anti-solvent may be in the range of from about 10:1 to about 1:10, suitably from 8:1 to 1:5, preferably from 6:1 to 1:1, when preparing a supercritical or subcritical fluid which is not totally solvent saturated.

The particles produced according to the present process, may be subsequently treated with a dry anti-solvent in a supercritical or subcritical state for obtaining particularly dry particles. It is however, preferred that use is made of fluid containing an anti-solvent, especially carbon dioxide, and a second solvent, which is water, also for subsequent conditioning of the particles formed, since this ensures that the substance in solvated form will mature into, and remain as, essentially crystalline particles. The supercritical or subcritical fluid contain-ing an anti-solvent and the second solvent, may be totally saturated with the solvent or exhibit a relative solvent saturation of the anti-solvent in the range of from about 50% up to 100%, i.e. total saturation, suitably in the range of from 90% up to 100%, and preferably in the range of from 95% up to 100% of total solvent saturation at the prevailing pressure and temperature.

The particles of the invention may contain one or more pharmacologically active substance(s) in a solvated form and/or one or more pharmaceutically acceptable excipients in a solvated form, both intended for use in mammals, preferably human beings.

The solvate is a hydrate, such as a monohydrate, dihydrate or trihydrate.

The first solvent used for dissolving the substance at issue, can be one or more organic solvents, optionally in mixture with one or more polar solvents such as water. The solvent may be a lower alkyl alcohol, such as methanol, ethanol, n-propanol, isopropanol, n-butanol, iso-butanol, sec-butanol or tert-butanol, an aldehyde, a ketone, such as acetone, an ester, dimethylsulfoxide (DMSO), or any mixture of any of these.

The pharmacologically active substance can be selected from the group consisting of solvates of β agonists, including short acting and long acting β1 and β2 agonists, glucocorticosteroids, anticholinergics, leukotriene antagonists and proteins and peptides, especially inhalable proteins and peptides, and any mixture thereof, especially a solvate of a β agonist and a glucocorticosteroid.

β agonists for use in the present invention include, without limitation, solvates of formoterol, salbutamol, rimiterol, fenoterol, reproterol, pirbuterol, bitolterol, salmeterol, clenbuterol, procaterol, broxaterol, picumeterol, mabuterol, terbutaline, isoprenaline, orciprenaline, adrenaline, and pharmaceutically acceptable esters, acetals, and salts, and any mixture thereof. Suitably, use is made of solvates of formoterol, or any pharmaceutically acceptable salt thereof.

Suitable pharmaceutically acceptable salts of formoterol include acid addition salts derived from inorganic and organic acids, for example the chloride, bromide, sulfate, phosphate, maleate, fumarate, tartrate, citrate, benzoate, 4-methoxybenzoate, 2- or 4-hydroxybenzoate, 4-chlorobenzoate, p-toluenesulphonate, methanesulphonate, ascorbate, acetate, succinate, lactate, glutarate, gluconate, tricarballylate, hydroxynaphthalene-carboxylate or oleate salts or solvates thereof. The pharmacologically active substance is preferably a solvate of formoterol fumarate, and most preferably formoterol fumarate dihydrate.

The glucocorticosteroid, if used in the invention, is preferably an anti-inflammatory glucocorticosteroid, e.g. for use in nasal or oral inhalation, or for use in the treatment of intestinal diseases such as inflammatory bowel diseases (IBD), Crohn's disease or ulcerative colitis. Examples of glucocorticosteroids which may be used in the present invention include any solvate of betamethasone, fluticasone (e.g. as propionate), budesonide, tipredane, dexamethasone, beclomethasone (e.g. as dipropionate), prednisolone, fluocinolone (e.g. as acetonide), triamcinolone (e.g. as acetonide), mometasone (e.g. as furoate), rofleponide, flumethasone, flunisolide, ciclesonide, deflazacort, cortivazol, 16α,17α-butylidenedioxy-6α,9α-difluoro-11β, 21-dihydroxy-pregna-1,4-diene-3,20-dione; 6α,9α-difluoro-11β-hydroxy-16α,17α-butylidenedioxy-17β-methylthio-androsta-4-ene-3-one; 16α,17α-butylidenedioxy-6α,9α-difluoro-11β-hydroxy-3-oxo-androsta-1,4-diene-17β-carbothioic acid S-methyl ester; methyl 9α-chloro-6α-fluoro-11β-hydroxy-16α-methyl-3-oxo-17α-propionyloxy-androsta-1,4-diene-17α-carboxylate; 6α,9α-difluoro-11β-hydroxy-16α-methyl-3-oxo-17α-propionyloxy-androsta-1,4-diene-17,β-carbothioic acid S-(2-oxo-tetrahydrofuran-3-yl) ester; optionally in their pure isomeric forms (where such forms exist), any solvate of any pharmaceutically acceptable ester, acetal or salt thereof, and any mixture of any of these.

Pharmaceutically acceptable excipients are e.g. carriers, additives and diluents, including antioxidants. Suitable pharmaceutically acceptable excipients include, without limitation, solvates of one or more natural or synthetic carbohydrate, such as a monosaccharides, disaccharides, trisaccharides, oligosaccharides, polysaccharides and polyols, and/or in the form of their pharmaceutically acceptable esters, acetals, or salts (where such derivatives exist). Examples of naturally occurring monosaccharides include glucose, fructose and galactose. Examples of naturally occurring disaccharides include sucrose (saccharose), trehalose, maltose, cellobiose and lactose. The disaccharide is preferably lactose, more preferably lactose monohydrate. Examples of naturally occurring trisaccharides include raffinose and melezitose. The polysaccharide may be cellulose, starch, dextrins or dextran, or chemical derivatives of any of these. The cellulose derivative is suitably a cellulose ether such as ethylcellulose (EC), ethylmethylcellulose (EMC), hydroxyethylcellulose (HEC), ethylhydroxymethylcellulose (EHMC), ethylhydroxyethylcellulose (EHEC), methylcellulose (MC), hydroxymethylcellulose (HMC), hydroxypropylcellulose (HPC), hydroxypropylmethylcellulose (HPMC) and carboxymethylcellulose (CMC), e.g. the sodium salt thereof. The polyol is preferably a sugar alcohol, which can be obtained by reducing various monosaccharides. For example, sorbitol and mannitol may be obtained by reducing glucose and mannose, respectively.

The pharmacologically active substance or substances may be premixed with one or more pharmaceutically acceptable excipients before the process of the invention is applied. This is especially advantageous if the active substance is highly potent. It is, however, also possible to prepare crystalline particles containing an active substance according to the present invention and mix them with suitable excipient (s) afterwards. In this case, the excipient particles may also be produced according to the present invention, using e.g. the SEDS technique, or may be produced by some other suitable technique. It is further possible to prepare crystalline particles containing one or more excipient(s) according to the present invention and mix them with particles containing one or more active substances afterwards. In this case, the particles containing an active substance may also be produced according to the present invention, or may be produced by some other suitable technique.

When the particles produced contain a pharmacologically active substance the particles are suitably in a finely divided form, preferably having a mass median diameter (MMD) (as measured using a Coulter counter) of less than about 20 μm, more preferably of less than 10 μm, and most preferably with an MMD in the range of from 1 to 6 μm. The particles may alternatively be in an ultra fine form, e.g. having an MMD of less than 1.0 μm.

When the particles produced contain one or more pharmaceutically acceptable excipient the particles may have a mass median diameter (MMD) (as measured using a Coulter counter) of less than about 100 μm, suitably of less than 50 μm, preferably with an MMD of less than 20 μm, and more preferably with an MMD of less than 10 μm.

The present process is carried out under supercritical or subcritical conditions. The precise conditions of operation are dependent e.g. upon the choice of anti-solvent. Table 1, lists the critical pressure ($P_c$) and critical temperature ($T_c$) for some anti-solvents.

TABLE 1

| Anti-solvent | $P_c$ (bar) | $T_c$ (° C.) |
| --- | --- | --- |
| Carbon dioxide | 74 | 31 |
| Nitrous oxide | 72 | 36 |
| Sulfur hexafluoride | 37 | 45 |
| Ethane | 48 | 32 |
| Ethylene | 51 | 10 |
| Xenon | 58 | 16 |
| Trifluoromethane | 47 | 26 |
| Chlorotrifluoromethane | 39 | 29 |

In practice, it may be preferable to maintain the pressure inside the substance vessel substantially above the relevant $P_c$ whilst the temperature is only slightly above the $T_c$. Generally, therefore, the pressure may be in the range of from about 10 up to about 300 bar higher than the relevant $P_c$, suitably in the range of from 20 up to 200 bar higher, and preferably be in the range of from 30 up to 100 bar higher than the relevant $P_c$. Generally, also, the temperature may be in the range of from about 5 up to about 50° C. above the relevant $T_c$, suitably in the range of from 10 up to 40° C. above, and preferably in the range of from 15 up to 30° C. above the relevant $T_c$.

With carbon dioxide, the pressure may be in the range of from about 80 up to about 400 bar, suitably in the range of from 100 to 250 bar, preferably in the range of from 110 to 150 bar whilst the temperature may be in the range of from about 35 up to about 80° C., suitably in the range of from 40 up to 70° C., preferably in the range of from 45 up to 60° C.

The solution of dissolved substance and the supercritical or subcritical fluid containing an anti-solvent and a solvent should be pumped through the particle-forming vessel for a period of time selected such that the desired particle characteristics are obtained. The period of time can be regulated by altering the pressure, temperature and/or flow rate. The solution and supercritical or subcritical fluid containing an anti-solvent and a solvent can be pumped for a period of time in the range of from about 5 min up to about 48 hours, suitably from 15 min up to 24 hours, preferably from 30 min up to 12 hours.

After the formation of particles in the particle-forming vessel, it is suitable to condition the particles formed by circulating the fluid containing an anti-solvent and a second solvent for an additional period of time. The anti-solvent can be circulated for an additional period of time in the range of from about 1 min up to about 12 hours, suitably from 5 min up to 6 hours, preferably from 10 min up to 3 hours.

Conveniently, the present process is carried out as a one-way process, i.e. the supercritical or subcritical fluid passes the conditioning vessel only once. It is, however, possible to recirculate the supercritical or subcritical fluid after essentially restoring the initial relative or total solvent saturation value before the fluid reenters the conditioning vessel.

An apparatus suitable for use as a conditioning vessel in the present process, must be able to withstand the pressure and temperature prevailing at the preselected supercritical or subcritical condition. Furthermore, the apparatus must be able to withstand the impact of the anti-solvent/solvent mixture at issue under supercritical or subcritical conditions.

According to the invention there is also provided a pharmaceutical formulation comprising one or more pharmacologically active substance(s) produced according to the present invention and one or more pharmaceutically acceptable excipient(s). Examples of such excipients include carriers such as carbohydrates e.g. in a solvated form, additives such as antioxidants, and diluents. The active substance(s) are preferably selected from the group consisting of solvates of β agonists, glucocorticosteroids, anticholinergics, leukotriene antagonists, proteins and peptides, and any mixture thereof.

The invention further provides particles produced according to the present process containing one or more pharmacologically active substance(s) selected from the group consisting of solvates of β agonists, glucocorticosteroids, anticholinergics, leukotriene antagonists, proteins and peptides, mixed with one or more pharmaceutically acceptable excipient(s), for use in the treatment of a respiratory disorder such as an allergic and/or inflammatory condition of the nose or lungs, e.g. chronic obstructive pulmonary disease (COPD), rhinitis or asthma, or for use in the treatment of intestinal diseases such as inflammatory bowel diseases (IBD), Crohn's disease or ulcerative colitis.

The invention further provides a method for treatment of an allergic and/or inflammatory condition of the nose or lungs by administering to a mammal, especially a human being, suffering from such a condition a therapeutically effective amount of a formulation containing one or more pharmacologically active substance(s) selected from solvates of β agonists, glucocorticosteroids, anticholinergics, leukotriene antagonists, proteins and peptides, mixed with one or more pharmaceutically acceptable excipient(s). More specifically, the invention provides a method for treatment of chronic obstructive pulmonary disease (COPD), rhintis, asthma or other allergic and/or inflammatory conditions, or for treatment of intestinal diseases such as inflammatory bowel diseases (IBD), Crohn's disease or ulcerative colitis by administering to a mammal, especially a human being, suffering from such condition a therapeutically effective amount of a formulation containing one or more pharmacologically active substance(s) selected from solvates of β agonists, glucocorticosteroids, anticholinergics, leukotriene antagonists, proteins and peptides.

The invention will be illustrated by the following examples which are not intended to limit the scope of the invention.

EXAMPLES

Comparative Example 1

Several experiments were performed with a SEDS apparatus wherein dry carbon dioxide was used as the anti-solvent during the whole process for crystallizing formoterol fumarate dihydrate.

Various solvents were utilized, including methanol, ethanol, isopropanol, acetone, acetonitrile, and dimethylsulfoxide (DMSO) as well as solvent mixtures such as water/methanol water/isopropanol, water/acetone. The pressure inside the particle-forming vessel was varied between 90 to 300 bar, and the temperature inside the oven was varied between 32 to 75° C.

When organic solvents such as alcohols or alcohol-water mixtures were used to crystallize formoterol fumarate dihydrate using the conventional SEDS technique with a dry anti-solvent, it resulted in the formation of agglomerated particles, and amorphous powders containing formoterol fumarate dihydrate. No crystalline formoterol fumarate dihydrate was obtained in these experiments.

Comparative Example 2

A further experiment was performed with the SEDS apparatus used in Comparative Example 1, wherein dry carbon dioxide was used as the anti-solvent during the whole process.

0.370 g of formoterol fumarate dihydrate was dissolved in 17 ml of a mixture containing 1% water and 99% methanol. The concentration was thus 2.0% (w/v). The pressure and temperature inside the particle-forming vessel were 150 bar and 40° C., respectively. The nozzle opening was 0.2 mm and dry carbon dioxide was used as the anti-solvent. The flow rate of carbon dioxide pumped through the nozzle was 18.0 ml/min while that of the solution was 0.3 ml/min. The solution was pumped for 60 min and 30 mg of substance was obtained.

X-ray analysis revealed that the substance was totally amorphous.

Example 3

An experiment was performed according to the invention using a modified SEDS apparatus, wherein totally water-saturated carbon dioxide was used as the anti-solvent for crystallizing formoterol fumarate dihydrate. The same anti-solvent was used for flushing the particle-forming vessel for a defined period of time after precipitation of the solvate. The system was subsequently rinsed with dry carbon dioxide.

Totally water-saturated carbon dioxide was used as anti-solvent and the obtained substance was conditioned using totally water-saturated carbon dioxide. 0.387 g formoterol fumarate dihydrate was dissolved in 19 ml methanol (the concentration was 2.0% w/v). The pressure and temperature inside the particle-formation vessel were 150 bar and 40° C., respectively. The flow rate of carbon dioxide pumped through the nozzle was 18.0 ml/min while that of the solution was 0.3 ml/min. The nozzle opening was 0.2 mm. The solution was pumped into the particle-formation vessel for 60 min and 0.290 g formoterol fumarate dihydrate was obtained. In this experiment totally water-saturated carbon dioxide was flushed through the particle-forming vessel after the end of the run. A rinsing period followed, wherein dry carbon dioxide equivalent to two volumes of the vessel was used.

The obtained powder was crystalline according to the X-ray analysis and its diffractogram corresponded to the dihydrate form of formoterol fumarate.

What is claimed is:

1. A process for the preparation of substantially crystalline particles of a substance in a solvated form, comprising the steps of:
   (a) dissolving the substance in a first solvent;
   (b) introducing into an apparatus the solution containing the dissolved substance together with a partly or wholly water-saturated supercritical or subcritical fluid comprising an antisolvent; and
   (c) recovering the substantially crystalline solvated particles formed.

2. The process according to claim 1, wherein the anti-solvent is carbon dioxide.

3. The process according to claim 1, wherein the temperature lies in the range from about 5° C. up to about 50° C. above the critical temperature of the anti-solvent.

4. The process according to claim 1, wherein the pressure lies in the range of from about 10 bar up to about 300 bar higher than the critical pressure of the anti-solvent.

5. The process according to claim 1, wherein the first solvent is an organic solvent.

6. The process according to claim 1, wherein the lower alkyl alcohol is selected from the group consisting of methanol, ethanol, n-propanol, isopropanol, n-butanol, isobutanol, sec-butanol, tert-butanol, and mixtures thereof.

7. The process according to claim 1, wherein before the supercritical or subcritical fluid is introduced in the particle-forming apparatus, the fluid is saturated with the solvent in the range from about 50% up to 100% of total solvent-saturation at the prevailing pressure and temperature.

8. The process according to claim 7, wherein the flow rate ratio between dry and totally solvent saturated anti-solvent lies in the range of from about 10:1 to about 1:10.

9. The process according to claim 1, wherein the particles produced have a mass median diameter of less than about 20 μm.

10. The process according to claim 1, wherein the substance in a solvated form is a pharmacologically active substance selected from the solvates of the group consisting of β-agonists, glucocorticosteroids, anticholinergics, leukotriene antagonists, proteins, peptides, and mixtures thereof.

11. The process according to claim 10, wherein the β-agonist in a solvated form is selected from the solvates of the group consisting of formoterol, salbutamol, rimiterol, fenoterol, reproterol, pirbuterol, bitolterol, salmeterol, clenbuterol, procaterol, broxaterol, picumeterol, mabuterol, terbutaline, isoprenaline, orciprenaline, adrenaline, pharmaceutically acceptable esters, acetals, and salts of these compounds, and mixtures thereof.

12. The process according to claim 10 or 11, wherein the pharmacologically active substance in a solvated form is a hydrate.

13. The process according to claim 11, wherein the pharmacologically active substance in a solvated form is formoterol fumarate dihydrate.

14. The process according to claim 1, wherein the substance in a solvated form is a pharmaceutically acceptable carbohydrate selected from the group consisting of solvates of monosaccharides, disaccharides, trisaccharides, oligosaccharides, polysaccharides, polyols, and mixtures thereof.

15. The process according to claim 14, wherein the carbohydrate in a solvated form is a hydrate.

16. The process according to claim 14 or 15, wherein the carbohydrate is lactose monohydrate.

17. A pharmaceutical formulation comprising one or more pharmacologically active substances in a solvated form produced according to the method of claim 1, and one or more pharmaceutically acceptable excipients.

18. The pharmaceutical formulation according to claim 17, wherein the pharmacologically active substance in a solvated form is selected from the solvates of the group consisting of β-agonists, glucocorticosteroids, anticholinergics, leukotriene antagonists, proteins, peptides, and mixtures thereof.

19. The pharmaceutical formulation according to claim 17 or 18, wherein the β-agonist in a solvated form is selected from the group consisting of solvates of formoterol, salbutamol, rimiterol, fenoterol, reproterol, pirbuterol, bitolterol, salmeterol, clenbuterol, procaterol, broxaterol, picumeterol, mabuterol, terbutaline, isoprenaline, orciprenaline, adrenaline, and pharmaceutically acceptable esters, acetals, and salts of these compounds, and mixtures thereof.

20. The pharmaceutical formulation according to claim 17, wherein the pharmacologically active substance in a solvated form is a hydrate.

21. The pharmaceutical formulation according to claim 20, wherein the pharmacologically active substance in a solvated form is formoterol fumarate dihydrate.

22. The pharmaceutical formulation according to claim 17, wherein the pharmaceutically acceptable excipient is a carbohydrate selected from the group consisting of monosaccharides, disaccharides, trisaccharides, oligosaccharides, polysaccharides, polyols, pharmaceutically acceptable solvates of these compounds, and mixtures thereof.

23. The pharmaceutical formulation according to claim 22, wherein the carbohydrate is in a solvated form.

24. The pharmaceutical formulation according to claim 22, wherein the carbohydrate is lactose monohydrate.

25. The pharmaceutical formulation according to claim 17, wherein the particles produced have a mass median diameter of less than about 20 $\mu$m.

26. A method for treatment of an allergic and/or inflammatory condition of the nose or lungs comprising administering to a mammal suffering from such a condition a therapeutically effective amount of the formulation according to claim 17.

27. A method for treatment of chronic obstructive pulmonary disease, rhinitis or asthma comprising administering to a mammal suffering from such a condition a therapeutically effective amount of the formulation according to claim 17.

28. A method for treatment of inflammatory bowel diseases, Crohn's disease or ulcerative colitis comprising administering to a mammal suffering from such a condition a therapeutically effective amount of the formulation according to claim 17.

29. The process according to claim 3, wherein the temperature lies in the range from about 15° C. to 30° C. above the critical temperature.

30. The process according to claim 4, wherein the pressure lies in the range from about 30 bar up to about 100 bar higher than the critical pressure.

31. The process according to claim 5, wherein the organic solvent is selected from the group consisting of lower alkyl alcohols, aldehydes, ketones, esters, ethers, and mixtures thereof.

32. The process according to claim 7, wherein the fluid is saturated with the solvent in the range from 90% up to 100% of the total solvent saturation.

33. The process according to claim 8, wherein the flow ratio lies in the range from 6:1 to 1:1.

34. The process according to claim 9, wherein the particles produced have a mass mean diameter of less than 10 $\mu$m.

35. The process according to claim 12, wherein the hydrate is a monohydrate, dihydrate, or trihydrate.

36. The process according to claim 12, wherein the pharmacologically active substance in a solvated form is formoterol fumarate dihydrate.

37. The process according to claim 15, wherein the hydrate is a monohydrate, dihydrate, or trihydrate.

38. The pharmaceutical formulation according to claim 20, wherein the hydrate is a monohydrate, dihydrate, or trihydrate.

39. The pharmaceutical formulation according to claim 23, wherein the solvated form is a hydrate.

40. The pharmaceutical formulation according to claim 38, wherein the hydrate is a monohydrate, dihydrate, or trihydrate.

41. The pharmaceutical formulation according to claim 25, wherein the particles have a mass mean diameter of less than 10 $\mu$m.

42. The process according to claim 1, wherein the temperature in step (b) lies in the range from about 5° C. up to about 50° C. above the initial temperature of the antisolvent, and the pressure lies in the range from about 10 bar to about 300 bar higher than the critical pressure of the antisolvent.

* * * * *

UNITED STATES PATENT AND TRADEMARK OFFICE
CERTIFICATE OF CORRECTION

PATENT NO.    : 6,461,642 B1                                                   Page 1 of 1
DATED         : October 8, 2002
INVENTOR(S)   : Bisrat et al.

It is certified that error appears in the above-identified patent and that said Letters Patent is hereby corrected as shown below:

Title page,
Item [56], References Cited, U.S. PATENT DOCUMENTS,
Add the following documents:
-- US 6,063,138, issued 5/2000 to Hanna et al.
US 5,562,923, issued 10/1996 to Trofast et al. --
FOREIGN PATENTS DOCUMENTS,
Add the following douments:
--EP 02677,332, issued 10/1995
WO 95/01221, issued 1/1995
WO 95/05805, issued 3/1995 --
OTHER PUBLICATIONS,
Add the following references:
-- Crystallization Process in Modified Supercritical Fluids", Palakodaty et al., World Congress on Particle Technology 3, 1998
"Supercritical Fluid Processing of Materials from Aqueous Solutions: The Application of SEDS to Lactose as a Model Substance", Pharmaceutical Research, vol. 15, no. 12, 1998 --

Column 8,
Line 48, "claim 1" should be -- claim 31 --.

Signed and Sealed this

Eleventh Day of February, 2003

JAMES E. ROGAN
*Director of the United States Patent and Trademark Office*